United States Patent
Fink et al.

(10) Patent No.: US 8,384,894 B2
(45) Date of Patent: Feb. 26, 2013

(54) SUPERIOR ANALYZER FOR RAMAN SPECTRA WITH HIGH ACCEPTANCE CONE, RESOLUTION, TRANSMISSION, AND QUANTUM EFFICIENCY, AND STRONG BACKGROUND REDUCTION

(75) Inventors: Manfred Fink, Austin, TX (US); Philip Varghese, Austin, TX (US); Jacek Borysow, Atlantic Mine, MI (US)

(73) Assignees: Board of Regents of the University of Texas System, Austin, TX (US); Michigan Technological University, Houghton, MI (US)

( * ) Notice: Subject to any disclaimer, the term of this patent is extended or adjusted under 35 U.S.C. 154(b) by 34 days.

(21) Appl. No.: 13/015,878

(22) Filed: Jan. 28, 2011

(65) Prior Publication Data

US 2011/0218431 A1    Sep. 8, 2011

Related U.S. Application Data

(60) Provisional application No. 61/299,555, filed on Jan. 29, 2010.

(51) Int. Cl.
*G01J 3/44*    (2006.01)
(52) U.S. Cl. ............................................. 356/301
(58) Field of Classification Search ............ 356/301; 600/431
See application file for complete search history.

(56) References Cited

U.S. PATENT DOCUMENTS

| | | | |
|---|---|---|---|
| 4,633,103 A | 12/1986 | Hyman et al. | |
| 5,754,288 A * | 5/1998 | Yamamoto et al. | 356/301 |
| 5,786,893 A | 7/1998 | Fink et al. | |
| 6,307,626 B1 | 10/2001 | Miles et al. | |
| 6,778,269 B2 | 8/2004 | Fink et al. | |
| 2009/0306527 A1* | 12/2009 | Kubo et al. | 600/532 |

OTHER PUBLICATIONS

International Search Report and Written Opinion for International Application No. PCT/US2011/022884 (mailed Oct. 31, 2011).

* cited by examiner

*Primary Examiner* — Tarifur Chowdhury
*Assistant Examiner* — Abdullahi Nur
(74) *Attorney, Agent, or Firm* — Ballard Spahr LLP

(57) ABSTRACT

A Raman analyzer for analyzing light emitted from a Raman cell is provided that has a beam splitter configured to split the light emitted from the Raman cell into a first beam and a second beam. An atomic vapor filter can be used to filter a Raman scattered line from the first beam and a chopper system can periodically interrupt the first and second beams that are directed towards a photo detector, which can convert light from the first and second beams into an electrical signal. The signal output from the photo detector can optionally be amplified, digitized, Fourier filtered, and/or subjected to Fourier analysis.

12 Claims, 1 Drawing Sheet

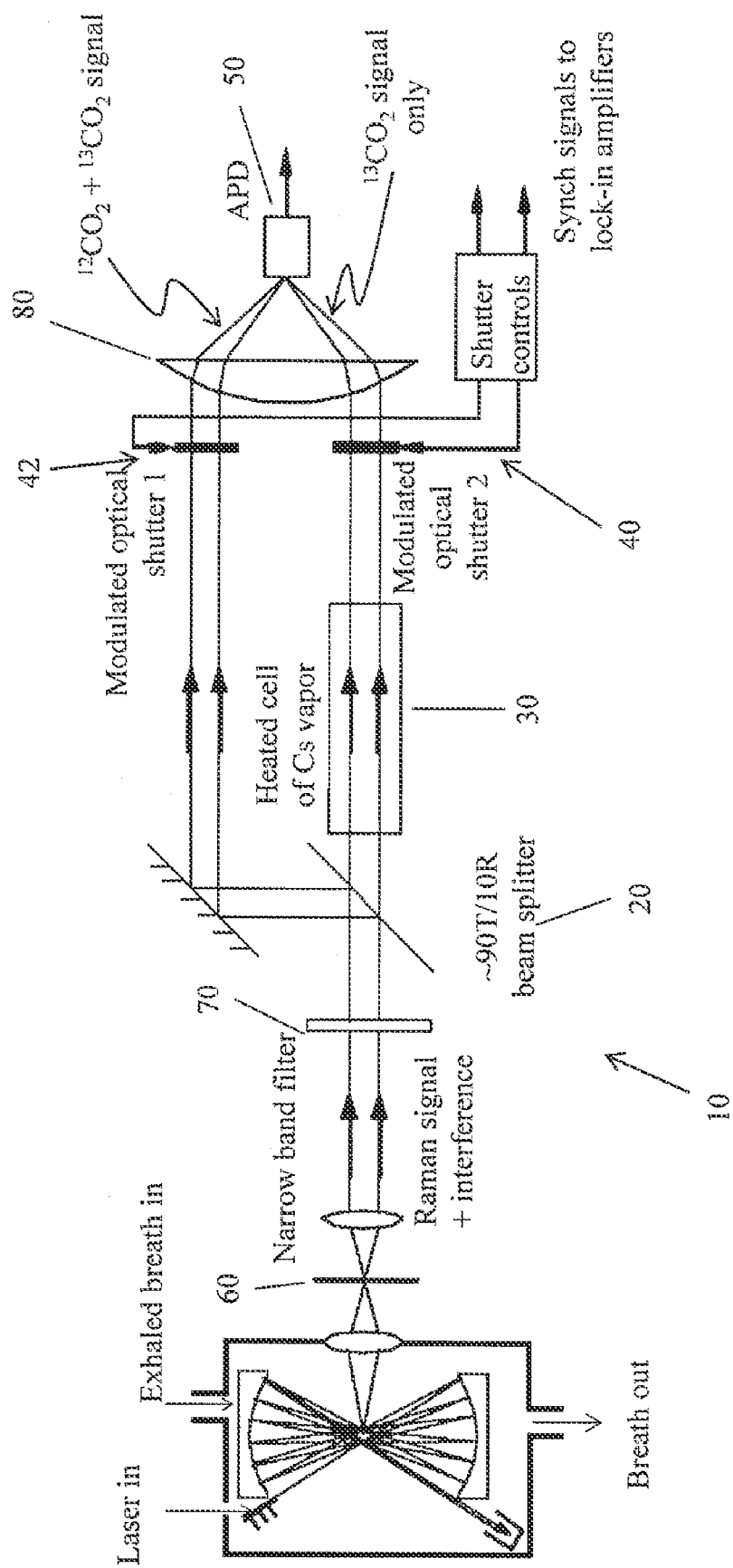

SUPERIOR ANALYZER FOR RAMAN SPECTRA WITH HIGH ACCEPTANCE CONE, RESOLUTION, TRANSMISSION, AND QUANTUM EFFICIENCY, AND STRONG BACKGROUND REDUCTION

CROSS-REFERENCE TO RELATED APPLICATIONS

This application claims priority to U.S. Provisional Patent Application Ser. No. 61/299,555 filed Jan. 29, 2010, which is hereby incorporated by reference in its entirety for all purposes.

This invention was made with government support under 0457194 awarded by National Science Foundation. The government has certain rights in the invention.

FIELD

Provided is a Raman spectral analyzer to measure the scattered light from a Raman cell. More specifically, a Raman spectral analyzer capable of measuring the isotope ratios of a plurality of compounds is provided.

BACKGROUND

Raman scattering is a type of inelastic scattering of electromagnetic radiation, such as visible light, discovered in 1928 by Chandrasekhara Raman. When a beam of monochromatic light is passed through a substance some of the radiation will be scattered. Although most of the scattered radiation will be the same as the incident frequency ("Rayleigh" scattering), some will have frequencies above ("anti-Stokes" radiation) and below ("Stokes" radiation) that of the incident beam. This effect is known as Raman scattering and is due to inelastic collisions between photons and molecules that lead to changes in the vibrational and rotational energy levels of the molecules. This effect is used in Raman spectroscopy for investigating the vibrational and rotational energy levels of molecules. Raman spectroscopy is the spectrophotometric detection of the inelastically scattered light.

"Stokes" emissions have lower energies (lower frequencies or a decrease in wave number ($cm^{-1}$)) than the incident laser photons and occur when a molecule absorbs incident laser energy and relaxes into an excited rotational and/or vibrational state. Each molecular species will generate a set of characteristic Stokes lines that are displaced from the excitation frequency (Raman shifted) whose intensities are linearly proportional to the density of the species in the sample.

"Anti-Stokes" emissions have higher frequencies than the incident laser photons and occur only when the photon encounters a molecule that, for instance, is initially in a vibrationally excited state due to elevated sample temperature. When the final molecular state has lower energy than the initial state, the scattered photon has the energy of the incident photon plus the difference in energy between the molecule's original and final states. Like Stokes emissions, anti-Stokes emissions provide a quantitative fingerprint for the molecule involved in the scattering process. This part of the spectrum is seldom used for analytical purposes since the spectral features are weaker. However, the ratio of the Stokes to the anti-Stokes scattering can be used to determine the sample temperature when it is in thermal equilibrium.

The Stokes and anti-Stokes emissions are collectively referred to as spontaneous "Raman" emissions. Since the excitation frequency (near infrared) and the frequency of the Stokes (and anti-Stokes) scattered light are typically far off the resonance of any component in the sample, fluorescence at frequencies of interest is minimal. The sample is optically thin and will not alter the intensities of the Stokes emissions (no primary or secondary extinctions), in stark contrast to infrared absorption spectroscopy.

Raman spectroscopy is a well-established technology to determine the presence of trace compounds and their isotopomers down to one part per million levels within a host of mixtures. With Raman analysis, absolute concentrations can be determined, the sparse spectra minimize interferences of overtones and combination lines because they are strongly suppressed.

However, conventional Raman spectrometers can require tuning of the incident laser frequency. Additionally, conventional Raman analyzers can lack the desired sensitivity, require an extensive integration time, be too large and/or be too costly for widespread use. Thus, there is a need in the art for a relatively inexpensive, compact Raman spectrometer capable of improved sensitivity and integration times, and capable of operating at high surrounding pressures (up to 800 bars).

SUMMARY

In accordance with the purpose(s) of this disclosure, as embodied and broadly described herein, in one aspect, a Raman analyzer for analyzing light emitted from a Raman cell is provided. In another aspect, the Raman analyzer can comprise a beam splitter configured to split the light emitted from the Raman cell into a first beam and a second beam. In another aspect, an atomic vapor filter can filter a Raman scattered line from the first beam. In further aspects, a chopper system can periodically interrupt the first and second beam and a photo detector can convert light from the first and second beams into an electrical signal. In another aspect, the signal output from the photo detector can be amplified, digitized and filtered to remove most of the background signal. Optionally, the final signal intensities can be recovered by digital lock-in analysis.

Additional advantages will be set forth in part in the description which follows, and in part will be obvious from the description, or may be learned by practice of the aspects of the disclosure as described herein. The advantages can be realized and attained by means of the elements and combinations particularly pointed out in the appended claims. It is to be understood that both the foregoing general description and the following detailed description are exemplary and explanatory only and are not restrictive of the aspects of the disclosure, as claimed.

BRIEF DESCRIPTION OF THE DRAWINGS

The features, nature, and advantages of the disclosed subject matter will become more apparent from the detailed description set forth below when taken in conjunction with the accompanying drawings, wherein:

FIG. 1 is a schematic diagram of a Raman analyzer, according to one aspect of the present disclosure.

DETAILED DESCRIPTION

The present disclosure may be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to an "analyzer" can include two or more such analyzers unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Reference will now be made in detail to certain embodiments of the disclosure, examples of which are illustrated in the accompanying drawings. Wherever possible, the same reference numbers are used throughout the drawings to refer to the same or like parts.

In one aspect, a Raman analyzer 10 is provided for analyzing the light emitted from a Raman cell, such as that described in U.S. Pat. No. 6,778,269, which is incorporated by reference herein in its entirety. As illustrated in FIG. 1, the analyzer 10, in one aspect, can comprise at least one of: a beam splitter 20, an atomic vapor filter 30, a chopper system 40, and a photo detector 50.

The beam splitter 20 can be a conventional beam splitter configured to split one beam of light into a plurality of beams. In one aspect, the beam splitter can be a polarization-sensitive beam splitter. In another aspect, the beam splitter can be a 90/10 beam splitter, wherein 90% of the original beam is split into a first beam of light, and 10% of the original beam is split into a second beam. In various other aspects, the beam splitter can be an 80/20 beam splitter, a 70/30 beam splitter, a 60/40 beam splitter, a 50/50 beam splitter and the like. In use, and as described more fully below, the second beam generates a constant standard against which the first beam can be normalized, and thus, all variation in the detector, such as power variations, can cancel when the ratios of the two signals are analyzed.

In another aspect, the atomic vapor filter 30 can be configured to substantially remove a particular Raman scattered line (Stokes emission) without attenuating other spectrally proximate Raman lines. Thus, the dominant line of a compound can be removed by the vapor filter and the remaining lines can pass completely. In one aspect, the atomic vapor filter can selectively absorb an isotope based on a frequency of the light passing through the filter. In another aspect, the atomic vapor filter 30 comprises a glass cell filled with, for example and without limitation, a monatomic vapor, such as cesium. In another aspect, the vapor may be chosen to have an absorption resonance at a frequency equal to the frequency of the laser source minus the frequency of a particular target molecule's Raman shift, which is the frequency of a Raman line that is spectrally close to another Raman line. It is of course contemplated that the atomic vapor filter can be heated. Other atomic vapors can be used in place of cesium in the atomic vapor filter medium, in combination with suitably chosen laser light sources. For example and without limitation, another metal vapor or a noble gas may be employed as the filter medium, as well as an ionic doped glass, with a corresponding monochromatic light source chosen to produce a beam at a frequency selected to filter a particular Raman line. In another aspect, the atomic filter can separate down to the Doppler widths of the sample and the vapor of the atomic filter.

The chopper system 40, in one aspect, can comprise a plurality of optical interrupters 42 configured to selectively block the first and/or second beams of light, thereby selectively preventing the first and/or second beams from traveling past the optical interrupters. In another aspect, each optical interrupter can comprise a shutter configured to modulate with incommensurable frequency. Optionally, it is contemplated that the shutters can modulate at a random frequency or constantly at a predetermined frequency. For example, a shutter of a first optical interrupter can modulate with a frequency of 100 Hz and a shutter of a second optical interrupter can modulate with a frequency of 47 Hz. In still another aspect, the chopper system can comprise a shutter control system configured to control the modulation of the shutters.

In one aspect, the photo detector 50 can comprise at least one conventional photo detector configured to convert light into an electrical signal. In another aspect, the photo detector 50 can comprise a single conventional photo detector configured to convert light into an electrical signal. In another aspect, the photo detector can comprise a photo diode. In still another aspect, the photo detector 50 can comprise an avalanche photodiode. In another aspect, the photo detector can convert light from the first beam into a first electrical signal, and light from the second beam into a second electrical signal.

In one aspect, the electrical signal output from the photo detector 50 can be sent to at least one conventional amplifier for amplification. In another aspect, the at least one amplifier can comprise at least one digital lock-in amplifier. In still another aspect, the shutter control system of the optical interrupters can be synchronized with the at least one amplifier so that at a particular instance, the signal received by the amplifier can be matched with the appropriate first or second beam. In another aspect, the first electrical signal can be compared to the second electrical signal (from the unfiltered second beam) to normalize the first electrical signal. In still another aspect, the amplified signal output from the at least one amplifier can be digitized and Fourier filtered to remove most of the background signal. In another aspect, the final signal intensities can be recovered by electronic digital lock-in analysis.

In use, light scattered from a Raman cell, as described in U.S. Pat. No. 6,778,269 can be collected with a large acceptance cone and filtered by a pinhole-filter 60 to filter the light emitted from a specific volume in the Raman cell (the Raman signal) and to output a beam having a smooth transverse intensity profile.

In one aspect, the photons of the light output from the pinhole filter are focused to infinity crossing a narrow band-pass filter 70 at a right angle which can set the spectral window of interest and filter out interference from the Raman signal. In another aspect, the center wavelength of the narrow band-pass filter can coincide with the wavelength of the D1 line of the vapor, for example, cesium (894.35 nm), of the atomic vapor filter. The light is split into the first beam and the second beam with the beam splitter 20. In one aspect, the first beam of light crosses the vapor filter 30 which can remove the strong Raman line of the abundant compound (e.g., $^{12}CO_2$ from $^{13}CO_2$), by setting the incident primary laser wavelength, $\lambda$, of a laser input into the Raman cell appropriately.

For example, the lower branch of the Fermi dyad of $CO_2$, λ of the laser is tuned to 795.779 nm. In this aspect, the neighboring weaker Raman line (for $^{13}CO_2$, 893.0 nm) lies within the window of the narrow band-pass filter 70 and can pass through the vapor filter 30 fully, independent of incident angles. In another aspect, the second beam can remain unfiltered by the atomic vapor filter.

In one exemplary aspect, the light of both the first and second beams can be chopped by the optical interrupters 42 operating at the incommensurable frequency and can be focused with a lens 80 onto the photo-detector 50. In still another aspect, light input into the photo detector can be converted into an electrical signal that, after amplification, can be digitized and Fourier filtered to remove at least a portion of the background signal to produce a final signal. Optionally, it is contemplated that the final signal intensities can be recovered by electronic digital lock-in analysis.

In one aspect, the analyzer 10 can measure the isotope ratio of other compounds simultaneously by altering the diode laser that produces the light emitted from the Raman cell to a laser having a desired wavelength. The signals from all compounds retain their identification by the use of an optical chopper and an additional set of lock-in amplifiers in front of the Raman cell so that at a particular instance, the light emitted from the Raman cell can be matched with the appropriate compound.

In one aspect, after the system is set up with the desired laser diode, no tuning or adjustment is needed for all compounds to be analyzed. Tuning will be required only at the onset of its use, given by each compound to be investigated. In another aspect, the analyzer of the current application can require no calibrations, has a very large dynamic intensity range, low dependence on the temperature of the surrounding, can measure several compounds simultaneously and has Doppler width limited resolution. In another aspect, the resolution of the instrument is set by the Doppler width of the vapor filter 30. In another aspect, the large acceptance angle, the high through-put, as well as the high quantum efficiency of the photodetector and the strong background reduction of the instant Raman analyzer can yield improved sensitivity when compared to conventional Raman analyzers. In another aspect, when compared to conventional Raman analyzers, the instant Raman analyzer 10 can record data for all compounds under investigation with shorter integration times. It is also contemplated that due to the use of affordable, accessible components, the analyzer of the current application can minimize the fabrication costs. In still another aspect, the analyzer 10 can be small in size and thus readily portable with the use of batteries to supply power.

In certain aspects, the Raman analyzer 10 can be used to non-invasively test for the conversion of an isotopically labeled substrate, such as for example and without limitation, $^{12}CO_2$, $^{13}CO_2$, $NH_4{}^{14}NO_3$, $NH_4{}^{13}NO_3$, $H_2$, HD, $D_2$, and the like. Optical spectroscopy provides a common diagnostic tool to evaluate patients' health problems without the use of X-rays, whole body scans with radioactive markers, blood samples or biopsies.

In one aspect, a method of diagnosing a health problem in a patient by a health care provider comprises using the Raman analyzer 10 to determine an isotope ratio of exhaled human breath. In another aspect, the isotope ratio of exhaled human breath can be the $^{12}CO_2/^{13}CO_2$ ratio. In another aspect, after a patient has been administered an organic, $^{13}C$-isotope enriched compound that decomposes with high probability at the site to be investigated, the presence of certain diseases can be determined.

In one aspect, the method of diagnosing a health problem further comprises administering a $^{13}C$-isotope-labeled compound which decomposes at a specific site in the body. Breath exhaled from humans typically contains about 7 mbar $CO_2$ ($2.2 \cdot 10^{17}$ molecules/cm$^3$) of which about 1% is $^{13}CO_2$. The decomposition products will contain $CO_2$ which will be all $^{13}CO_2$. The added contribution to the $^{13}CO_2/^{12}CO_2$ ratio varies as a function of time since the administered dose was digested by the patient. In one aspect, the isotope ratio of $^{12}CO_2/^{13}CO_2$ as a function of time can provide direct conclusions concerning the status of a disease. Repeated checkups can show the evolution of the healing process or progression of the disease. In one example, $^{13}C$-labeled urea ($NH_2{}^{13}CONH_2$) can be used to detect the presence of *Helicobacter pylori* in the mucus of the upper gastrointestinal tract. In another aspect, at least ten different diseases can be identified by the $^{13}C$-isotope breath analysis using Raman spectroscopy.

Thus, in one aspect, it is contemplated that the analyzer 10 of the current application can diagnose a patient's healing process without radioactive substances or biopsies and with a short analysis time. The compounds used can be harmless (i.e., are not radioactive) and are acceptable for children and pregnant women. In one aspect, each patient measurement time period can be about 2 hours and can deliver substantially instant results.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A Raman analyzer for analyzing light emitted from a Raman cell, comprising:
   a beam splitter configured to split the light emitted from the Raman cell into a first beam and a second beam;
   an atomic vapor filter configured to remove a Raman scattered line from the first beam;
   a chopper system configured to periodically interrupt the first and second beam; and
   a photo detector configured to convert light from the first and second beams into an electrical signal.

2. The analyzer of claim 1, wherein the beam splitter is a 90/10 beam splitter such that the first beam comprises 90% of the light input into the beam splitter, and the second beam comprises 10% of the light input into the beam splitter.

3. The analyzer of claim 1, wherein the atomic vapor filter comprises a cesium vapor filter.

4. The analyzer of claim 1, wherein the chopper system periodically interrupts the first and second beam with incommensurable frequency.

5. The analyzer of claim 1, wherein the photo detector is an avalanche photo diode.

6. The analyzer of claim 1, further comprising a pinhole filter to filter the light emitted from the Raman cell and to output a beam of light having a smooth transverse intensity profile.

7. The analyzer of claim 6, further comprising a narrow band-pass filter configured such that its center wavelength coincides with the wavelength of the D1 line of atomic vapor, wherein the beam of light output from the pinhole filter is passed through the narrow-band pass filter, and wherein the light output from the narrow band-pass filter is output to the beam splitter.

8. The analyzer of claim 7, further comprising a lens configured to focus the first and second beams of light onto the photo detector.

9. The analyzer of claim 8, wherein light input into the photo detector is output as an electrical signal that is amplified by at least one amplifier.

10. The analyzer of claim 9, wherein the amplified signal is digitized and Fourier filtered to remove most of the background signal to produce a final signal.

11. The analyzer of claim 10, wherein the final signal intensities are recovered by electronic digital lock-in analysis.

12. A method for analyzing light emitted from a Raman cell, comprising:
    splitting light emitted from the Raman cell into a first beam and a second beam;
    filtering the first beam to remove a Raman scattered line;
    interrupting periodically the first and second beam;
    converting light from the first beam into a first electrical signal;
    converting light from the first beam into a second electrical signal;
    comparing the first electrical signal to the second electrical signal to normalize the first electrical signal, and recovering normalized signal intensity by electronic digital Fourier analysis.

\* \* \* \* \*